(12) United States Patent
Kaeppeli

(10) Patent No.: US 9,931,299 B2
(45) Date of Patent: Apr. 3, 2018

(54) BIOMASS HETERO-COLLOIDAL SYSTEMS, PRODUCTION AND USES THEREOF

(71) Applicant: Othmar Kaeppeli, Würenlos (CH)

(72) Inventor: Othmar Kaeppeli, Würenlos (CH)

( * ) Notice: Subject to any disclaimer, the term of this patent is extended or adjusted under 35 U.S.C. 154(b) by 4 days.

(21) Appl. No.: 14/394,798

(22) PCT Filed: Apr. 19, 2013

(86) PCT No.: PCT/EP2013/058150
§ 371 (c)(1),
(2) Date: Oct. 16, 2014

(87) PCT Pub. No.: WO2013/156587
PCT Pub. Date: Oct. 24, 2013

(65) Prior Publication Data
US 2015/0050323 A1   Feb. 19, 2015

(30) Foreign Application Priority Data

Apr. 20, 2012 (CH) .......................... 547/12

(51) Int. Cl.
| | | |
|---|---|---|
| A61K 9/14 | (2006.01) |
| A61K 36/899 | (2006.01) |
| A23L 1/052 | (2006.01) |
| A61K 8/02 | (2006.01) |
| A61K 8/96 | (2006.01) |
| A23K 1/14 | (2006.01) |
| A61K 36/06 | (2006.01) |
| A61K 36/74 | (2006.01) |
| C12N 1/14 | (2006.01) |
| A23F 5/10 | (2006.01) |
| A61Q 19/00 | (2006.01) |
| A61K 8/97 | (2017.01) |
| A61K 8/99 | (2017.01) |
| A23K 10/10 | (2016.01) |
| A23K 10/37 | (2016.01) |
| A23K 50/80 | (2016.01) |
| A23L 29/206 | (2016.01) |
| A23L 7/10 | (2016.01) |
| A23L 31/00 | (2016.01) |
| A23L 33/10 | (2016.01) |
| A23L 33/105 | (2016.01) |
| A23L 33/135 | (2016.01) |
| A23L 33/14 | (2016.01) |
| A23L 33/15 | (2016.01) |
| A61K 8/9706 | (2017.01) |

(52) U.S. Cl.
CPC .................. *A61K 9/14* (2013.01); *A23F 5/10* (2013.01); *A23K 10/10* (2016.05); *A23K 10/37* (2016.05); *A23K 50/80* (2016.05); *A23L 7/115* (2016.08); *A23L 29/206* (2016.08); *A23L 31/00* (2016.08); *A23L 33/10* (2016.08); *A23L 33/105* (2016.08); *A23L 33/135* (2016.08); *A23L 33/14* (2016.08); *A23L 33/15* (2016.08); *A61K 8/0241* (2013.01); *A61K 8/96* (2013.01); *A61K 8/97* (2013.01); *A61K 8/9706* (2017.08); *A61K 8/99* (2013.01); *A61K 36/06* (2013.01); *A61K 36/74* (2013.01); *A61K 36/899* (2013.01); *A61Q 19/00* (2013.01); *C12N 1/14* (2013.01); *A23V 2002/00* (2013.01); *A61K 2800/10* (2013.01)

(58) Field of Classification Search
None
See application file for complete search history.

(56) References Cited

U.S. PATENT DOCUMENTS

| | | | |
|---|---|---|---|
| 1,415,469 | A | 5/1922 | Plauson |
| 4,204,005 | A | 5/1980 | Kudo et al. |
| 5,185,175 | A | 2/1993 | Loh et al. |
| 6,214,337 | B1 | 4/2001 | Hayen et al. |
| 2009/0048208 | A1* | 2/2009 | Byun .................. C07H 1/00 514/54 |

FOREIGN PATENT DOCUMENTS

| | | | |
|---|---|---|---|
| CN | 1265291 | | 9/2000 |
| CN | 1748568 | | 3/2006 |
| WO | WO1999003356 | * | 1/1999 |
| WO | 00/07715 | | 2/2000 |

OTHER PUBLICATIONS

Tofu, dried-frozen (kayadofu), prepared with calcium sulfate (Jan. 14, 2011).*
Ringgenberg, Elise "The Physico-Chemical Characterization of Soymilk Particles and Gelatin Properties of Acid-Induced Soymilk Gels, as a Function of Soymilk Protein Concentration" Oct. 2011.*

(Continued)

*Primary Examiner* — Robert A Wax
*Assistant Examiner* — Danah Al-Awadi
(74) *Attorney, Agent, or Firm* — Wenderoth, Lind & Ponack, L.L.P.

(57) ABSTRACT

Disclosed herein are inventive stable homogenized biomass hetero-colloids, their production and uses. Such biomass hetero-colloids comprise biomass derived solid particle colloid matter and at least 15% (w/w) biomass derived soluble colloid matter. The novel biomass hetero-colloids provide an inventive approach for the application of biologically active compounds. Bio-actives are made available in an innovative form involving low intervention processing and enhancing the biological availability.

6 Claims, No Drawings

(56) References Cited

OTHER PUBLICATIONS

Li et al. Composition, Nutrition, and Utlization of Okara, (Soybean Residue) Jun. 2011.*
Hisotry of Soy Flber and Dietary Fiber (1621-2013). 2013.*
International Search Report issued Sep. 12, 2013 in International (PCT) Application No. PCT/EP2013/058150.
Written Opinion issued Sep. 12, 2013 in International (PCT) Application No. PCT/EP2013/058150.
Knuckles et al., "β-Glucan-Enriched Fractions from Laboratory-Scale Dry Milling and Sieving of Barley and Oats", Cereal Chemistry, vol. 69, No. 2, 1992, pp. 198-202.
Verlhac et al., "Immunomodulation by dietary vitamin C and glucan in rainbow trout (*Oncorhynchus mykiss*)", Fish & Shellfish Immunology, vol. 8, 1998, pp. 409-424.
Huang et al., "Evaluation of glucan/poly(vinyl alcohol) blend wound dressing using rat models", International Journal of Pharmaceutics, vol. 346, Jun. 2007, pp. 38-46.
Chan et al., "The effects of β-glucan on human immune and cancer cells", Journal of Hematology & Oncology, vol. 2, p. 25, 2009.
Moelants et al., "A Review on the Relationships between Processing, Food Structure, and Rheological Properties of Plant-Tissue-Based Food Suspensions", Comprehensive Reviews in Food Science and Food Safety, vol. 13, 2014, pp. 241-260.
Result of Consultation issued Dec. 12, 2017 in corresponding European Application No. 13 719 450,2.

\* cited by examiner

BIOMASS HETERO-COLLOIDAL SYSTEMS, PRODUCTION AND USES THEREOF

FIELD OF INVENTION

The present invention relates to novel homogenized biomass hetero-colloids, a process of their production, and the use of such biomass hetero-colloids.

BACKGROUND

A colloid is matter microscopically dispersed evenly throughout another substance (from Wikipedia, the free encyclopaedia. Retrieved 18 Apr. 2012). Colloidal systems consist of two separate phases: a dispersed phase (or internal phase) and a continuous phase (or dispersion medium) in which the colloid is dispersed. A colloidal system may be solid, liquid, or gaseous.

Another distinct property of colloidal systems is the size of the dispersed phase solids. They have a diameter between approximately 1 and 1,000 nanometers. Colloids of dispersed solid phases with particle sizes larger than 1 micrometer belong to the category of micro-colloidal systems.

Colloidal systems are prepared by homogenizing energy input dispersing large particles to the colloidal dimensions. Grinding and milling techniques are commonly used for subdivision of large solid particles. The methods are capable to disperse particles to a size, which is a result of equilibrium between the two processes: subdivision and aggregation under mechanical force.

The application of biomass or biomass derived products (e.g. from herbs) has become progressively more popular in animal and human nutrition as well as in cosmetics and medicine. Their use relates to the fact that biomass, in particular of microbial, fungal and plant origin, contain active ingredients, so called bio-actives, which denote substances that have an effect on living systems (for a review see Ncube et al., African Journal of Biotechnology, 7, 1797-1806, 2008).

Although the effects of bio-actives have not always been formally and scientifically researched, their popularity is based on a long track record validating their safety and efficacy. With recent advances in medical and nutrition sciences, natural products and health-promoting foods have received extensive attention from both health professionals and the general population. Increasing knowledge from food chemistry, nutritional, and clinical studies is providing more insight into our understanding of biological functions, usage, and potential adverse effects of bio-actives. This advanced knowledge also calls for standardized manufacturing processes and clinical practices and at the same time could add more value to bio-active markets.

When applying bio-actives in animal and human nutrition or in cosmetics an important issue is whether to use the whole biomass or whether to supply the bio-actives in standardized extracts from biomass. A standardized extract contains one or more bio-active components in a specific, guaranteed amount. The intention behind the standardization is to guarantee that the consumer is getting a product in which the quality is consistent from batch to batch.

Unfortunately, while scientists can isolate many constituents from biomass and discover how particular chemicals may act in the body, they inadvertently remove or overlook components that may contribute to the activity of the whole biomass. Consequently, standardization may concentrate one constituent at the expense of other potentially important ones, while changing the natural balance of the bio-actives in the entire biomass.

Standardization, therefore, is based on the idea that isolated compounds are responsible for the bio-activity of biomass. In fact, biomass contains a complex blend of bio-actives. The full bio-active value of biomass is most likely due to their internal complexity and to the interactions of the different components within the body rather than to one of its specific components.

Furthermore, many of the constituents of biomass are as yet unknown and internal chemical interactions within and among biomass are even more poorly understood. Therefore, application of isolated enriched bio-actives may not be advisable and it is doubtful that this type of standardized biomass extracts can exhibit the same full spectrum of activity as the whole biomass. However, science has proven the efficacy of some of these concentrated extracts regarding specific biological activities, so they can be very useful even if they do not work exactly like whole biomass.

SUMMARY OF THE INVENTION

The invention relates to a stable homogenized biomass hetero-colloid of solid particle colloid matter and at least 15% (w/w), preferably 30% (w/w) soluble colloid matter, in particular such hetero-colloid wherein the median size of the solid particle colloid matter is in the range of 1 to 500 micrometers. The invention likewise relates to this biomass hetero-colloid in dried form.

Furthermore the invention relates to a process of manufacture of the mentioned hetero-colloids, characterized in that a suspension of biomass is homogenized, yielding a stable biomass hetero-colloid characterized by an increased percentage of soluble colloid matter.

Furthermore the invention relates to the use of the homogenized biomass hetero-colloid in different fields.

DETAILED DESCRIPTION OF THE INVENTION

The current invention discloses an inventive approach for the application of bio-actives of a particular biomass. The inventive homogenized biomass hetero-colloidal systems are a novel form of biomass, allowing administration of all bio-actives of the biomass, and involving a low intervention processing, thus preserving the naturalness of the bio-actives and enhancing the biological availability.

In the present invention the colloid is biomass, which does not yield a single type of dispersed phase upon homogenization of a suspension thereof, but a combination of solid particles with increased amounts of soluble colloid matter. The inventive colloidal systems contain, among other cellular compounds of biomass, soluble fibre, the soluble colloid matter forming macromolecular assemblies of soluble polymers (e.g. hemicelluloses), and insoluble fibre, the solid particle colloid matter (e.g. cellulose, lignin) giving rise to the formation of liquid—solid and liquid—liquid colloidal fractions. Therefore the inventive biomass derived colloidal systems are referred to as hetero-colloidal systems. The invention relates to a homogenized biomass hetero-colloid of solid particle colloid matter and of at least 15% (w/w), preferably at least 30% (w/w) soluble colloid matter.

The mean particle size of the solid particles of the current invention is above 1 micrometer, predominantly in the range from 1 to 500 micrometers whereby the size distribution of any particular biomass colloid follows a Gaussian distribution. This is in contrast to the usual size distribution of solids in colloids of between 1 and 1000 nanometers. Consequently the inventive biomass hetero-colloids belong to the category of micro-colloidal systems. As a consequence the appearance of biomass hetero-colloids is milky.

The rationale behind biomass hetero-colloidal system preparation is (1) breaking up trapping cellular structures of biomass thus unblocking the release of (active) biomass ingredients into the continuous phase or the dispersed phases of the hetero-colloidal system, (2) solubilizing loosely bound or cross-linked polymers (polysaccharides, proteins) by the homogenizing energy input thus adding soluble colloid matter to the soluble colloid matter released upon suspension of the biomass colloid, and (3) down-sizing the solid biomass particles and consequently increasing interfacial area for mass transfer of any (active) biomass ingredient of the solid phase with the continuous phase or the soluble colloid phase. These features of the novel homogenized biomass hetero-colloids make them equivalent or more advantageous for the delivery of bio-actives in any animal, human, cosmetic and medicinal application as compared to standardized bio-active extracts.

The preparation of inventive biomass hetero-colloids basically involves the homogenization of an aqueous suspension of micron-sized and micronized native or dry biomass respectively. For the purposes of this invention, "micron-sized" biomass relates to any type of unicellular biomass or aggregates thereof. For the purpose of this invention "micronized" biomass relates to fungal, plant or animal biomass which in a first step is micronized by any mean but preferably by dry milling. "Micronized" is equivalent to "finely commuted".

Homogenization of the micron-sized and micronized aqueous biomass suspensions, respectively, is achieved by the dispersion of large particles to the colloidal dimensions. Biomass concentration of the initial suspension is between 0.1 and 30% but preferably between 1 and 10%. For homogenization energy input techniques like ultrasonic, pressure and mechanical treatments are applied. Transfer of large particles to the colloidal dimensions is most efficiently achieved by wet milling with a bead/ball mill. The properties of the resulting novel biomass hetero-colloidal system are determined by the operating conditions of the homogenization. Operating parameters of a bead/ball mill homogenization influencing biomass hetero-colloidal system properties are: Biomass concentration, energy input (agitation speed), bead size, gas content, temperature, and residence time. By varying these parameters the resulting biomass hetero-colloidal systems exhibit low to high viscosity (paste-like).

The invention further relates to dried homogenized biomass hetero-colloids, obtainable by removal of water from the described homogenized biomass hetero-colloids. Water may, for example, be removed by freeze-drying. The dry homogenized biomass hetero-colloids may be stored and transported in this form, and later be reconstituted with water to provide the original hetero-colloids.

The invention further relates to a process of production of a stable homogenized biomass hetero-colloid characterized in that the percentage of soluble colloid matter is increased by homogenizing a 0.1 to 30% aqueous suspension of said biomass. The amount of soluble colloid matter is increased to at least 15% (w/w of total biomass applied), preferably to at least 30% (w/w of total biomass applied) by this process. Homogenisation is achieved by the mentioned methods, in particular by high energy wet milling with a bead/ball mill.

The invention further relates to a process of production of a dried homogenized biomass hetero-colloid characterized in that the amount of soluble colloid matter is increased to at least 15% (w/w), preferably to at least 30% (w/w) by homogenizing a 0.1 to 30% aqueous suspension of said biomass, followed by removal of water.

Characteristic Features of Inventive Homogenized Biomass Hetero-colloidal Systems Hetero-colloid relevant components of biomass are: insoluble fibre consisting of solid particle forming polymers like lignin, polysaccharides such as cellulose, glucan, and chitin; soluble fibre like plant hemicelluloses such as pectin, arabinogalactan, microbial polysaccharides such as mannan, animal polysaccharides such as chitin, and proteins. The former and mixtures thereof constitute the solid particle colloid matter, the latter and mixtures thereof constitute the soluble colloid matter.

Consequently biomass hetero-colloidal systems consist of a solid and a liquid dispersed phase which may capture biomass compounds that are insoluble in the continuous phase or exhibit a higher affinity to any of the dispersed phases like many bio-actives contained in the biomass or any bio-active additionally added keeping them suspended in the aqueous continuous phase. Therefore the inventive biomass hetero-colloidal systems form an ideal method for the presentation of bio-actives from biomass or of such externally added in human and animal nutrition as well as in cosmetics and medicine.

Optional Components of Inventive Homogenized Biomass Hetero-colloidal Systems

As biomass hetero-colloidal systems are not fully loaded by biomass derived bio-actives the solid particle colloid matter and the soluble colloid matter may also serve as carriers or suspension aids, respectively, for additionally added functional ingredients like vitamins, extracted phytochemicals or any type of cosmetic and medicinal active compounds, in particular amphiphilic and hydrophobic compounds.

Similarly any soluble (polymeric) or solid (e.g. insoluble fibre, nano particles) colloid matter may be additionally added. Optional components are added to the biomass suspension before homogenization or mixed with micron-sized and micronized dry biomass, respectively, before suspension and subsequent homogenization.

Uses of Homogenized Biomass Hetero-colloidal Systems

Generally homogenized biomass hetero-colloidal systems can be used in all applications where bio-actives, for example phytochemicals or prebiotic plant polysaccharides, are used in animal and human nutrition, in cosmetic formulations and in medicine. Preparation of hetero-colloidal systems by homogenization breaks up the cellular structures of the biomass and releases structurally trapped biomass compounds such as proteins, lipids, polysaccharides, carotenoids, antimicrobials and antioxidants. By transferring biomass rich in compounds particularly valuable for health, like herbs or medicinal plants, into a homogenized hetero-colloid, bio-active ingredients become available in various forms adequate to the nature of the compounds. They may dissolve in the continuous aqueous phase, adsorb to the solid particle colloid matter or form a suspension with the aid of the soluble colloid matter. Consequently hetero-colloidal systems may present bio-actives for an optimal bioavailability. Furthermore homogenization of the biomass enhances the interfacial area which gives rise to an improved mass transfer, for example with respect to intestinal absorption or skin penetration in nutritional and cosmetic applications, respectively. Particularly useful are biomass hetero-colloidal systems for the feeding of larval fish and crustaceans. They perfectly support the uptake of nutrition by filter feeders.

The possibility to load homogenized biomass hetero-colloidal systems with additional biologically active substances makes them ideal as carriers in nutritional, cosmetic and medicinal applications. In particular lipophilic or amphiphilic compounds become available in an aqueous environment, subsequently yielding a phased release due to the partitioning of such substances between the solid particle matter and the soluble colloid matter, respectively.

EXAMPLE 1

Yeast Glucan Hetero-colloid

Yeast glucan (>85% purity) was isolated according to Freimund et al. (Carbohydrate Polymers, 54, 159-171, 2003). Analytics were done according to Freimund et al. (Eur Food Res Technol, 220, 101-105, 2005).

55 g of this yeast glucan was suspended in 945 g of water. The suspension was stirred and then an aliquot of the suspension was centrifuged (Heraeus Biofuge primo, at 8500 rpm corresponding to 10,000×g for 3 min) for soluble colloid matter determination in the supernatant.

Glucan soluble colloid matter after suspension: 1.9 g (3.5%)

Glucan solid particle colloid matter after suspension: 49.2 g (89.5%)

To prepare a homogenized yeast glucan hetero-colloid according to the invention, the original product was treated by high energy homogenization under the following conditions:
Homogeniser: 0.6 l DynoMill® KDL
Polyurethane agitator disk diameter: 64 mm
Glass beads: 500 ml, 0.5-0.7 mm diameter
Width of exit slit: 0.2 mm
Homogenization energy input: 3000 rpm corresponding to a tip speed of 10 m/s
Flow rate: 20 l/h
Exposure time: 30 min by recycling the suspension
Operating temperature: 20-40° C.

After homogenization an aliquot was submitted to centrifugation for the determination of the effect of homogenization on soluble colloid matter formation.

Appearance of glucan hetero-colloidal system: Stable, milky

Glucan soluble colloid matter after homogenisation: 9.7 g (17.7%)

Glucan solid particle colloid matter after homogenisation: 39.4 g (72.7%)

Glucan soluble colloid matter released by homogenizing: 7.8 g (14.2%)

Size of glucan solid particle colloid matter: >90% in the range of 0.5 to 10 micrometers with a mean particle size of 5.0 micrometers being the prevalent fraction.

The yeast glucan hetero-colloid may be used as addition to drinks or incorporation into cosmetic formulations.

EXAMPLE 2

Fungal Mycelium Hetero-colloid 50 g of finely ground mycelium from *Aspergillus niger*, a by-product of citric acid production, was suspended in 950 g of water. The suspension was stirred and then an aliquot of the suspension was centrifuged (Heraeus Biofuge primo, at 8500 rpm corresponding to 10,000×g for 3 min) for soluble colloid matter determination in the supernatant.

Fungal mycelium soluble colloid matter after suspension: 2.6 g (5.2%)

Fungal mycelium solid particle colloid matter after suspension: 47.4 g (94.8%)

To prepare a homogenized fungal mycelium hetero-colloid according to the invention, the product was treated by high energy homogenization under the following conditions:
Homogeniser: 0.6 l DynoMill® KDL
Polyurethane agitator disk diameter: 64 mm
Glass beads: 500 ml, 0.5-0.7 mm diameter
Width of exit slit: 0.2 mm
Homogenization energy input: 3000 rpm corresponding to a tip speed of 10 m/s
Flow rate: 20 l/h
Exposure time: 30 min by recycling the suspension
Operating temperature: 20-40° C.

After homogenization an aliquot was submitted to centrifugation for the determination of the effect of homogenization on soluble colloid matter formation.

Appearance of fungal mycelium hetero-colloidal system: Stable, milky, brownish

Total soluble colloid matter after homogenisation: 19.2 g (38.3%)

Total solid particle colloid matter after homogenisation: 30.8 g (61.6%)

Soluble colloid matter released by homogenizing: 16.6 g (33.2%)

The fungal mycelium hetero-colloid may be used as prebiotic feed additive, and as whole fungal mycelium powder after drying.

EXAMPLE 3

Maitake Mushroom (*Grifola frondosa*) Hetero-colloid 50 g of finely ground powder of fruiting bodies from *Grifola frondosa* were suspended in 950 g of water. The suspension was stirred and then an aliquot of the suspension was centrifuged (Heraeus Biofuge primo, at 8500 rpm corresponding to 10,000×g for 3 min) for soluble colloid matter determination in the supernatant.

Maitake mushroom soluble colloid matter after suspension: 25.2 g (50.3%)

Maitake mushroom solid particle colloid matter after suspension: 24.8 g (49.7%)

To prepare a homogenized maitake mushroom hetero-colloid according to the invention, the product was treated by high energy homogenization under the following conditions:
Homogeniser: 0.6 l DynoMill® KDL
Polyurethane agitator disk diameter: 64 mm
Glass beads: 500 ml, 0.5-0.7 mm diameter
Width of exit slit: 0.2 mm
Homogenization energy input: 3000 rpm corresponding to a tip speed of 10 m/s
Flow rate: 20 l/h
Exposure time: 30 min by recycling the suspension
Operating temperature: 20-40° C.

After homogenization an aliquot was submitted to centrifugation for the determination of the effect of homogenization on soluble colloid matter formation.

Appearance of the maitake mushroom hetero-colloidal system: Stable, brownish

Total soluble colloid matter after homogenisation: 39.2 g (78.3%)

Total solid particle colloid matter after homogenisation: 10.8 g (21.7%)

Soluble colloid matter released by homogenizing: 14.0 g (28.0%)

The soluble colloidal matter of the maitake mushroom (*Grifola frondosa*) hetero-colloid may be used as substitute for mushroom extract.

EXAMPLE 4

Oat Bran Hetero-colloid 40 g of finely ground powder of oat bran was suspended in 960 g of water. The suspension was stirred and then an aliquot of the suspension was centrifuged (Heraeus Biofuge primo, at 8500 rpm corresponding to 10,000×g for 3 min) for soluble colloid matter determination in the supernatant.

Oat bran soluble colloid matter after suspension: 5.2 g (13%)

Oat bran solid particle colloid matter after suspension: 33.2 g (87%)

To prepare a homogenized oat bran hetero-colloid according to the invention, the product was treated by high energy homogenization under the following conditions:
Homogeniser: 0.6 l DynoMill® KDL
Polyurethane agitator disk diameter: 64 mm
Glass beads: 500 ml, 0.5-0.7 mm diameter
Width of exit slit: 0.2 mm
Homogenization energy input: 3000 rpm corresponding to a tip speed of 10 m/s
Flow rate: 20 l/h
Exposure time: 30 min by recycling the suspension
Operating temperature: 20-40° C.

After homogenization an aliquot was submitted to centrifugation for the determination of the effect of homogenization on soluble colloid matter formation.

Appearance of the oat bran hetero-colloidal system: Stable, white to greyish

Oat bran soluble colloid matter after homogenisation: 13.8 g (34.6%)

Oat bran solid particle colloid matter after homogenization: 26.2 g (65.4%)

Oat bran soluble colloid matter released by homogenizing: 8.6 g (21.6%)

The oat bran hetero-colloid may be used as oat bran drink.

EXAMPLE 5

Coffee Bean Hetero-colloid 50 g of finely ground powder of roasted coffee beans was suspended in 950 g of water. The suspension was stirred at room temperature and then an aliquot of the suspension was centrifuged (Heraeus Biofuge primo, at 8500 rpm corresponding to 10,000×g for 3 min) for soluble colloid matter determination in the supernatant.

Total soluble colloid matter after suspension: 3.2 g (6.4%)

Total solid particle colloid matter after suspension: 46.8 g (93.6%)

To prepare a homogenized coffee bean hetero-colloid according to the invention, the product was treated by high energy homogenization under the following conditions:
Homogeniser: 0.6 l DynoMill® KDL
Polyurethane agitator disk diameter: 64 mm
Glass beads: 500 ml, 0.5-0.7 mm diameter
Width of exit slit: 0.2 mm
Homogenization energy input: 3000 rpm corresponding to a tip speed of 10 m/s
Flow rate: 20 l/h
Exposure time: 30 min by recycling the suspension
Operating temperature: 20-40° C.

After homogenization an aliquot was submitted to centrifugation for the determination of the effect of homogenization on soluble colloid matter formation.

Appearance of the coffee bean hetero-colloidal system: Stable, dark brown to black Total soluble colloid matter after homogenisation: 26.7 g (53.4%)

Total solid particle colloid matter after homogenization: 24.3 g (46.6%)

Total soluble colloid matter released by homogenizing: 23.5 g (47.0%)

The coffee bean hetero-colloid may be used as coffee drink.

EXAMPLE 6

Yeast Glucan Hetero-colloid Loaded with Vitamin E

A biomass hetero-colloidal system was prepared by suspending 30 g of glucan from example 1 and 5 g of vitamin E in 965 g of water. The suspension was stirred and then an aliquot of the suspension was centrifuged (Heraeus Biofuge primo, at 8500 rpm corresponding to 10,000×g for 3 min) for soluble Vitamin E determination in the aqueous supernatant.

Vitamin E in aqueous phase after suspension: <1 mg (vitamin E is virtually insoluble in water)

For high energy homogenization the following conditions were applied:
Homogeniser: 0.6 l DynoMill® KDL
Polyurethane agitator disk diameter: 64 mm
Glass beads: 500 ml, 0.5-0.7 mm diameter
Width of exit slit: 0.2 mm
Homogenization energy input: 3000 rpm corresponding to a tip speed of 10 m/s
Flow rate: 20 l/h
Exposure time: 30 min by recycling the suspension
Operating temperature: 20-40° C.

After homogenization an aliquot was submitted to centrifugation for the determination of the effect of homogenization on soluble and solid colloid matter and on Vitamin E content of the aqueous phase.

Appearance of glucan/vitamin E hetero-colloidal system: Stable, milky

Vitamin E in soluble glucan colloid matter (aqueous phase) after homogenisation: 0.02 g Vitamin E in solid glucan particle colloidal matter (solid phase) after homogenisation: 4.6 g.

The yeast glucan hetero-colloid loaded with vitamin E may be used as aqueous formula of vitamin E, as food additive and in cosmetic formulations.

The invention claimed is:

1. A homogenized biomass hetero-colloid consisting of an aqueous continuous phase and a dispersed phase,
   wherein the dispersed phase consists of a biomass hetero-colloid consisting of:
      a liquid-solid colloidal fraction comprising solid particle colloid matter consisting of insoluble fibre, and
      a liquid-liquid colloidal fraction comprising soluble colloid matter comprising soluble fibre forming macromolecular assemblies of soluble polymers, wherein the soluble colloid matter represents at least 15% (w/w) of the biomass prior to the homogenization; and wherein
said homogenized biomass hetero-colloid is obtained by high energy wet milling with a bead/ball mill of a 0.1 to 30% aqueous suspension of said biomass at a temperature of 20-40° C., wherein said biomass is micron-sized unicellular organisms or aggregates thereof, or of micronized fungal, plant or animal origin.

2. The biomass hetero-colloid of claim 1, wherein the soluble colloid matter represents at least 30% (w/w) of the biomass prior to the homogenization.

3. The biomass hetero-colloid of claim 1, wherein the mean particle size of the solid particle colloid matter is in the range of 1 to 500 micrometers.

4. A dried homogenized biomass hetero-colloid of claim 1 obtainable by removal of water.

5. A process of producing a stable homogenized biomass hetero-colloid consisting of an aqueous continuous phase and a dispersed phase, wherein the dispersed phase consists of a biomass hetero-colloid consisting of:
a liquid-solid colloidal fraction comprising solid particle colloid matter consisting of insoluble fibre, and
a liquid-liquid colloidal fraction comprising at least 15% (w/w) soluble colloid matter comprising soluble fibre forming macromolecular assemblies of soluble polymers,
the process comprising homogenizing a 0.1 to 30% aqueous suspension of the biomass until a liquid-solid colloidal fraction and a liquid-liquid colloidal fraction comprising soluble colloid matter is formed, wherein the soluble colloid matter represents at least 15% (w/w) of said biomass prior to homogenization, and wherein said biomass is micron-sized unicellular organisms or aggregates thereof, or of micronized fungal, plant or animal origin, and wherein said homogenisation is by wet milling with a bead/ball mill.

6. A process of producing a dried homogenized biomass hetero-colloid, comprising obtaining the stable homogenized biomass hetero-colloid produced by the process of claim 5, and removing water.

* * * * *